United States Patent [19]

Park et al.

[11] Patent Number: 5,691,278

[45] Date of Patent: Nov. 25, 1997

[54] OXAZOLINONE DERIVATIVES, PROCESS FOR PREPARING THE SAME, AND USE OF THE SAME

[75] Inventors: Sang Woo Park; Kye Jung Shin; Dong Chan Kim, all of Seoul, Rep. of Korea

[73] Assignee: Korea Institute of Science and Technology, Seoul, Rep. of Korea

[21] Appl. No.: 515,608

[22] Filed: Aug. 16, 1995

[30] Foreign Application Priority Data

Aug. 17, 1994 [KR] Rep. of Korea .................. 20300/1994

[51] Int. Cl.$^6$ ................................................. C07D 263/22
[52] U.S. Cl. .................... 504/252; 504/270; 546/271.4; 548/228
[58] Field of Search .......................... 504/252, 270; 546/271.4; 548/228

[56] References Cited

PUBLICATIONS

Jones, T.R. et al., "Quinazoline Antifolates Inhibiting Thymidylate Synthase: Variation of the Amino Acid", J.Med.Chem., 29, pp. 1114–1118, 1986.

Toniolo, C. et al, "A Long, Regular Polypeptide 3(10)–Helix", Macromolecules, 19, pp. 472–479, 1986.

Primary Examiner—C. Warren Ivy
Assistant Examiner—Lyman H. Smith
Attorney, Agent, or Firm—Townsend and Townsend and Crew

[57] ABSTRACT

An oxazolinone derivative compound, represented by the general formula I, shows superior herbicidal activity against, especially, dicotyledonous vegetables. It is effective upon applying both before and after the sprouting of vegetables. It is prepared by condensating an α-amino acid represented by the general formula II with an acid chloride represented by the general formula III, to give an acyl α-amino acid represented by the following formula IV: reacting the acyl α-amino acid with acetic anhydride; and dehydrating the resulting adduct:

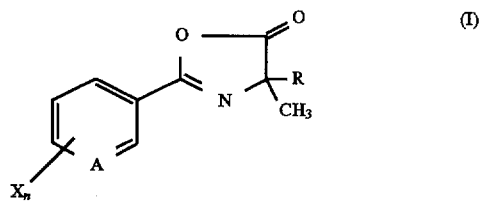

(I)

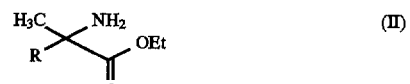

(II)

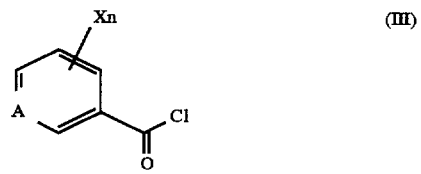

(III)

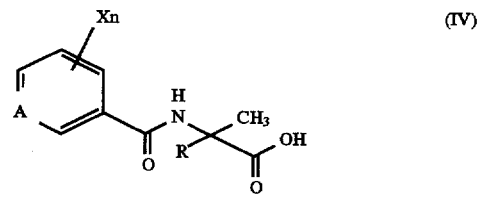

(IV)

wherein, R represents a lower alkyl group or a phenyl group containing halogen, lower alkyl or trifluoromethyl group; X represents halogen atom, carbomethoxy group, nitro group, or halogen or trifluoromethyl-substituted phenoxy group, being the same or different from one another; A represents nitrogen or carbon atom; and n is an integer of 1 to 3.

6 Claims, No Drawings

OXAZOLINONE DERIVATIVES, PROCESS FOR PREPARING THE SAME, AND USE OF THE SAME

BACKGROUND OF THE INVENTION

The present invention relates to novel oxazolinone derivatives, process for preparing the same, and use as a herbicide.

It is known that there exist no herbicides with the structure of oxazolinone.

SUMMARY OF THE INVENTION

The present invention provides oxazolinone derivatives represented by the following general formula I:

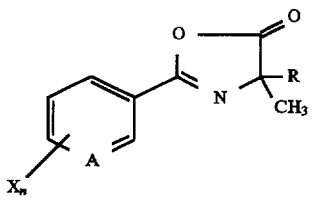

wherein, R represents a lower alkyl group or a phenyl group containing halogen, lower alkyl or trifluoromethyl group; X represents halogen atom, carbomethoxy group, nitro group, or halogen or trifluoromethyl-substituted phenoxy group, being the same or different from one another; A represents nitrogen or carbon atom; and n is an integer of 1 to 3.

The present invention also provides a process for preparing the novel oxazolinone derivatives. In the process, important is an α-amino acid derivative which is substituted at the α position. Such derivative may be prepared by various procedures including the hydrolysis (as the case may be) of the hydantoins derived from ketones for which a synthesis is described in J. Org. Chem., 1960, 25, p 1920, by Goodson et al, as shown in the following Reaction Chart.

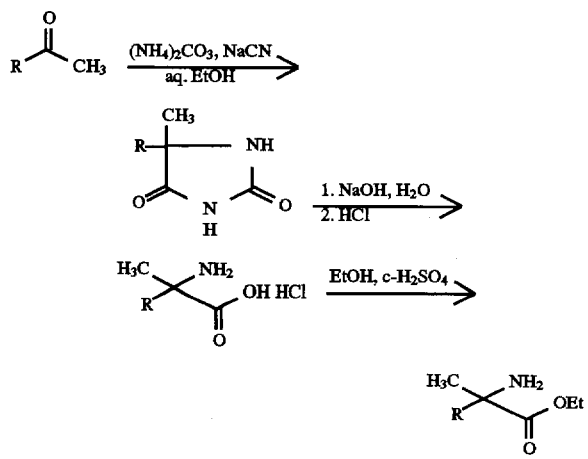

R: a lower alkyl or substituted phenyl.

Accordingly, the present process for preparing the novel oxazolinone derivatives represented by the formula I comprises the steps of condensating an α-amino acid represented by the following general formula II:

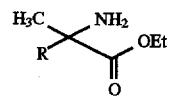

wherein R represents a lower alkyl group or a phenyl group containing halogen, lower alkyl or trifluoromethyl group, with an acid chloride represented by the following formula III:

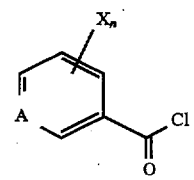

wherein X represents halogen atom, carbomethoxy group, nitro group, or halogen or trifluoromethyl-substituted phenoxy group, being the same or different from one another, to give an acyl α-amino acid represented by the following formula IV:

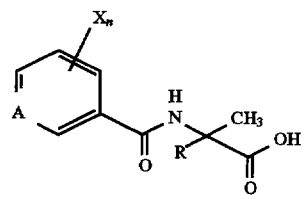

wherein, R is as defined above, A represents nitrogen or carbon atom, and n is an integer of 1 to 3; reacting the acyl α-amino acid with acetic anhydride; and dehydrating the resulting adduct.

DETAILED DESCRIPTION OF THE INVENTION

The novel oxazolinone derivatives of the present invention exhibit very useful herbicidity. Accordingly, the present invention also provides a herbicide containing the oxazolinone derivative as the effective ingredient.

Even when the herbicide is applied to crops after as well as before the sprouting, it is effective to them.

In most cases, pre-sprouting herbicides, if the crops are not sprouted, are scattered over the cultivated fields whenever prior to, during or subsequent to the sowing of the seeds of the crops, with the aim of treating of the soil. On the other hand, post-sprouting herbicides are applied during the growth periods of crops after the crops are sprouted. As mentioned previously, the herbicide of the present invention shows herbicidal effect for the crops irrespective of the application time. That is, it is effective whether the present herbicide is applied in the cultivated fields prior to or subsequent to the sprouting of the crops.

In more detail, the herbicide of the present invention shows better prevention of the breeding and extermination of wide-leaf weeds than Gramineae weeds, in dry fields. More particularly, it exhibits superior herbicidal activity against black nightshade (*Solanum nigrum* L.) and velvetleaf (*Abutilon avicennae* Gaertn) when it is applied to after the sprouting of crops while maintaining relative stability to Gramineae crops, especially, corn (*Zea mays* L.), wheat (*Triticum aestirum* L.) and rice (*Oryza sativa* L.). In rice paddy fields, it is preventive of the breeding and extermination of barnyardgrass (*Echinochloa crus-galli* P.BEZUV. var. *oryzicola* OHWI) and monochoria (*Monochoria vaginalis* PRESL.) and is little harmful to rice (*Oryza sativa* L). Therefore, the oxazolinone derivatives of the present invention are sufficiently useful as herbicidal ingredient.

A better understanding of the present invention may be obtained in light of following examples which are set forth to illustrate, but are not to be construed to limit, the present invention.

EXAMPLE I

Synthesis of Ethyl 2-(m-chlorobenzamido)-2-(p-tolyl)propionate 4.2 g (0.02M) of ethyl 2-amino-2-p-tolyl propionate and 3 g (0.03M) of triethylamine were dissolved in 40 ml of methylene dichloride. To this, 3.5 g (0.02M) of meta chlorobenzoyl chloride in 5 ml of methylene dichloride was slowly dropwise added. After being stirred for 1 hr at room temperature the resulting solution was washed with water and dried and removed the solvent, to give 6.5 g of the titled compound: 95 % Yield.

EXAMPLE II

Synthesis of 2-(m-chlorobenzamido)-2-(p-tolyl) propionic acid 1.2 g (0.02M) of potassium hydroxide was dissolved in a mixed solution of 30 ml of ethanol and 5 ml of $H_2O$. To this solution, 3.5 g (0.01M) of ethyl 2-(m-chlorobenzamido)-2-(p-tolyl)propionate obtained in Example I was added. The resulting solution was heated for 1 hr with reflux, cooled and distilled in vacuo to remove ethanol. The remainder was adjusted into pH 2 with 2 N HCl solution and extracted with methylene dichloride. Thereafter, the extract was distilled in vacuo, to give 2.9 g of the titled compound: 92 % Yield.

EXAMPLE III

Synthesis of 2-(m-chlorophenyl)-4-methyl-4-(p-tolyl)-oxazolin-5-one 3.17 g (0.01M) of 2-(m-chlorobenzamido)-2-(p-tolyl) propionic acid was dissolved in 30 ml of acetic anhydride and the resulting solution was heated for 1 hr with reflux. The reaction solution was cooled and distilled out acetic anhydride in vacuo. The residue was subjected to chromatography, to give 2.4 g of the object compound, pure oily compound: 80 % Yield.

NMR ($CDCl_3$) δ1.83 (s, 3H), 2.32 (s, 3H), 7.13–8.13 (m, 8 H)

Using the starting material and acid chloride as indicated in the following Table 1, 2 and 3, the compounds represented in the Table 1, 2 and 3 were obtained in the same manners as those of Examples I, II and III.

TABLE I

| Cpd. No. | X | Y | Z | R | NMR Data ($CDCl_3$) | Yield |
|---|---|---|---|---|---|---|
| 1 | Cl | H | H | p-Chlorophenyl | 1.79(s, 3H) 7.27–7.99(m, 8H) | 72% |
| 2 | H | Cl | H | p-Chlorophenyl | 1.80(s, 3H) 7.29–8.15(m, 8H) | 81% |
| 3 | H | Cl | H | m-Tolyl | 1.77(s, 3H) 2.33(s, 3H) 7.01–7.99(m, 8H) | 79% |
| 4 | H | H | Cl | m-Tolyl | 1.77(s, 3H) 2.32(s, 3H) 7.04–8.03(m, 8H) | 77% |
| 5 | H | H | Cl | p-Chlorophenyl | 1.83(s, 3H) 7.24–8.10(m, 8H) | 83% |
| 6 | Cl | H | Cl | p-Chlorophenyl | 1.85(s, 3H) 7.30–7.97(m, 7H) | 85% |
| 7 | H | Cl | H | p-Tolyl | 1.83(s, 3H) 2.32(s, 3H) 7.13–8.13(m, 8H) | 85% |
| 8 | H | H | Cl | p-Tolyl | 1.80(s, 3H) 2.21(s, 3H) 7.11–8.10(m, 8H) | 75% |
| 9 | $COOCH_3$ | H | H | isopropyl | 1.01(d, 3H) 1.11(d, 3H) 1.52(s, 3H), 2.03(dq, 1H) 3.88(s, 3H), 7.47–7.89(m, 4H) | 71% |
| 10 | $COOCH_3$ | H | H | m-Trifluoro-tolyl | 1.86(s, 3H) 3.08(s, 3H) 7.46–7.91(m, 4H) | 70% |
| 11 | $COOCH_3$ | H | H | $CH_3$ | 1.53(9, 6H) 3.86(s, 3H) 7.47–7.92(m, 4H) | 72% |
| 12 | $CCOCH_3$ | H | H | m-Chlorophenyl | 1.85(s, 3H) 3.82(s, 3H) 7.18–7.88(m, 8H) | 80% |
| 13 | $COOCH_3$ | H | H | m-Tolyl | 1.90(s, 3H) 2.39(s, 3H) 3.87(s, 3H) 7.26–8.04 | 83% |

TABLE II

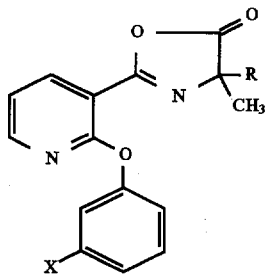

| Cpd. No. | X | Y | Z | R | NMR Data (CDCl$_3$) | Yield |
|---|---|---|---|---|---|---|
| 14 | Cl | H | Cl | m-Tolyl | 1.88(s, 3H) 2.35(s, 3H) 7.05–8.15(m, 10H) | 72% |
| 15 | Cl | H | Cl | m-Chloro-phenyl | 1.89(s, 3H) 7.05–8.12(m, 10H) | 81% |
| 16 | Cl | H | Cl | p-Chloro-phenyl | 1.87(s, 3H) 7.04–8.15(m, 10H) | 79% |
| 17 | H | CF$_3$ | H | m-Tolyl | 1.77(s, 3H) 2.32(s, 3H) 7.03–8.17(m, 11H) | 77% |
| 18 | H | CF$^2$ | H | m-Chloro-phenyl | 1.83(s, 3H) 7.05–8.18(m, 11H) | 83% |
| 19 | H | CF$_3$ | H | p-Tolyl | 1.85(s, 3H) 2.33(s, 3H) 7.05–8.16(m, 11H) | 85% |
| 20 | H | CF$_3$ | H | p-Chloro-phenyl | 1.84(s, 3H) 7.06–8.19(m, 11H) | 85% |
| 21 | Cl | H | CF$_3$ | isopropyl | 0.98(d, 3H) 1.13(d, 3H) 1.49(s, 3H) 2.15(m, 1H) 7.01–8.16(m, 6H) | 71% |
| 22 | Cl | H | CF$_3$ | m-Trifluoro-tolyl | 1.89(s, 3H) 6.98–8.17(m, 10H) | |
| 23 | Cl | H | CF$_3$ | m-Tolyl | 1.87(s, 3H) 2.37(s, 3H) 7.03–8.18(m, 10H) | 70% |
| 24 | Cl | H | CF$_3$ | m-Chloro-phenyl | 1.87(s, 3H) 7.01–8.17(m, 10H) | 72% |
| 25 | Cl | H | CF$_3$ | p-Chloro-phenyl | 1.87(s, 3H) 7.02–8.16(m, 10H) | 80% |
| 26 | Cl | H | CF$_3$ | p-Tolyl | 1.85(s, 3H) 2.32(s, 3H) 7.00–8.14(m, 10H) | 83% |

TABLE III

| Cpd. No. | X | R | NMR DATA (CDCl$_3$) | Yield |
|---|---|---|---|---|
| 27 | CF$_3$ | m-Tolyl | 1.88(s, 3H) 2.36(s, 3H) 7.09–7.66(m, 9H) 8.32–8.44(m, 2H) | 82% |
| 28 | CF$_3$ | m-Chloro-phenyl | 1.88(s, 3H) 7.16–7.71(m, 9H) 8.36–8.48(m, 2H) | 79% |
| 29 | CF$_3$ | p-Tolly | 1.85(s, 3H) 2.33(s, 3H) 7.12–7.62(m, 9H) 8.33–8.45(m, 2H) | 85% |
| 30 | CF$_3$ | p-Chloro-phenyl | 1.86(s, 3H) 7.09–7.71(m, 9H) 8.33–8.45(m, 2H) | 90% |
| 31 | Cl | m-Tolyl | 1.89(s, 3H) 2.37(s, 3H) 7.14–7.62(m, 9H) 8.39–8.50(m, 2H) | 77% |
| 32 | Cl | m-Chloro-phenyl | 1.88(s, 3H) 7.12–7.69(m, 9H) 8.37–8.46(m, 2H) | 83% |
| 33 | Cl | p-Tolyl | 1.86(s, 3H) 2.35(s, 3H) 7.11–7.65(m, 9H) 8.33–8.45(m, 2H) | 85% |
| 34 | Cl | p-Chloro-phenyl | 1.86(s, 3H) 7.09–7.77(m, 9H) 8.32–8.47(m, 2H) | 82% |

EXAMPLE IV

Herbicidal Activity Assay

Sterilized sandy soil mixed with a proper amount of manure was put into test pots (348 cm$^2$). After holes were formed, test weed or crop seeds (common sorghum (Sorghum bicolor Moench), Branyardgrass (Echinochloa crus-galli P. Beauv), Japanese bromegrass (Thunb. ex Murr.), large crabgrass (Digitaria sangunalis (L.) Scop.), fall pandicum (Panicum dichotomiflorum Michx.), bindweed (Calystegia japonica Choisy), cocklebur (Xanthium strumarium L.), velvetleaf (Abutilon avicennae Gaetn), Indian jointvetch (Aeschynomene indica L.), black nightshade (Solanum nigrum L.), corn (Zea mays L.), soybean (Glycine max (L.) Merr.), cotton (Gossypium hirsumm L.), wheat (Triticum aestirum L.) rice (Oryza sativa L.) were sown in the holes. Subsequently, the seeds were covered with fine soils and the test pots were put in a greenhouse.

After being weighed, each of the test compounds (Compound Nos. 14 and 15 in Table 1) was diluted with water containing a nonionic surfactant (Tween-20), to a ratio of 1:1. The diluted solutions were sprayed at 14 ml per㎡. The herbicide formulations were sprayed one day after the sowing, for the pre-sprouting soil treatment and 8–12 days after the sowing, for the post-sprouting light leaf treatment.

Since then, the crops were further grown for 2–3 weeks. Based on morphological and physiological observation, the herbicidal effects on the vegetation were examined. In this test, the herbicidal activity was graded into 11 levels from 0 of no protection to 100 of perfect protection. The grades of not less than 70 were in practice regarded as to be effective to the vegetables. The results are given as shown in the following Table 4.

TABLE IV-1

Herbicidity Test

| Cpd. No. | Type | kg/ha | ZEAMX | GLXMA | GOSHI | TRZAW | ORYSA | SORBI | ECHCG |
|---|---|---|---|---|---|---|---|---|---|
| 14 | Pre- | 2 | 0 | 0 | 20 | 0 | 0 | 0 | 0 |
|  | Sprouting | .5 | 0 | 0 | 0 | 0 | 0 | 0 | 0 |
|  | Treatment | .125 | 0 | 0 | 0 | 0 | 0 | 0 | 0 |
|  |  | .03 | 0 | 0 | 0 | 0 | 0 | 0 | 0 |
|  | Post- | 2 | 15 | 40 | 100 | 30 | 10 | 20 | 20 |
|  | Sprouting | .5 | 10 | 20 | 80 | 20 | 0 | 10 | 10 |
|  | Treatment | .125 | 0 | 20 | 50 | 10 | 0 | 0 | 0 |
|  |  | .03 | 0 | 10 | 30 | 0 | 0 | 0 | 0 |
| 15 | Pre- | 2 | 0 | 0 | 30 | 0 | 0 | 0 | 0 |
|  | Sprouting | .5 | 0 | 0 | 0 | 0 | 0 | 0 | 0 |
|  | Treatment | .125 | 0 | 0 | 0 | 0 | 0 | 0 | 0 |
|  |  | .03 | 0 | 0 | 0 | 0 | 0 | 0 | 0 |
|  | Post- | 2 | 20 | 40 | 100 | 40 | 10 | 20 | 20 |
|  | Sprouting | .5 | 10 | 30 | 80 | 20 | 0 | 10 | 10 |
|  |  | .125 | 10 | 25 | 60 | 10 | 0 | 10 | 0 |
|  |  | .03 | 0 | 20 | 40 | 10 | 0 | 0 | 0 |

TABLE IV-2

Herbicidity Test

| Cpd. No. | Type | kg/ha | BROJA | DIGSA | PANDI | SOLNI | AESIN | ABUTH | XANSI | CACHE |
|---|---|---|---|---|---|---|---|---|---|---|
| 14 | Pre- | 2 | 0 | 0 | 0 | 100 | 80 | 30 | 10 | 60 |
|  | Sprouting | .5 | 0 | 0 | 0 | 0 | 0 | 20 | 0 | 0 |
|  | Treatment | .125 | 0 | 0 | 0 | 0 | 0 | 0 | 0 | 0 |
|  |  | .03 | 0 | 0 | 0 | 0 | 0 | 0 | 0 | 0 |
|  | Post- | 2 | 20 | 20 | 50 | 100 | 90 | 100 | X | 50 |
|  | Sprouting | .5 | 0 | 0 | 20 | 100 | 90 | 100 | X | 50 |
|  | Treatment | .125 | 0 | 0 | 0 | 80 | 80 | 100 | X | 20 |
|  |  | .03 | 0 | 0 | 0 | 70 | 65 | 30 | X | 10 |
| 15 | Pre- | 2 | 0 | 0 | 0 | 100 | 100 | 70 | 20 | 65 |
|  | Sprouting | .5 | 0 | 0 | 0 | 60 | 10 | 20 | 0 | 30 |
|  | Treatment | .125 | 0 | 0 | 0 | 0 | 0 | 0 | 0 | 0 |
|  |  | .03 | 0 | 0 | 0 | 0 | 0 | 0 | 0 | 0 |
|  | Post- | 2 | 10 | 20 | 60 | 100 | 100 | 100 | X | 100 |
|  | Sprouting | .5 | 10 | 0 | 40 | 100 | 100 | 100 | X | 100 |
|  | Treatment | .125 | 0 | 0 | 0 | 100 | 100 | 100 | X | 40 |
|  |  | .03 | 0 | 0 | 0 | 70 | 50 | 30 | X | 30 |

X: untested.

As apparent from Table IV, the oxazolinone derivatives of the present invention are very effective in removing the vegetables even at small amounts, showing better herbicidal effects upon application after than before the sprouting. In addition, the data shows that the herbicidal effect on the monocotyledonous vegetables (corn, soybean, cotton, wheat, rice, common sorghum and branyardgrass) is larger than that on the dicotyledonous vegetables (fall panicum, black nightshade, Indian jointvetch, velvetleaf, and bindweed).

Other features, advantages and embodiments of the present invention disclosed herein will be readily apparent to those exercising ordinary skill after reading the foregoing disclosures. In this regard, while specific embodiments of the invention have been described in considerable detail, variations and modifications of these embodiments can be effected without departing from the spirit and scope of the invention as described and claimed.

What is claimed is:

1. An oxazolinone derivative compound represented by the following formula I:

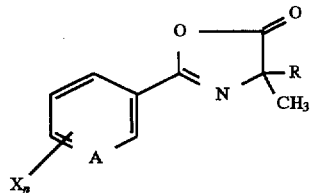

wherein, R represents a lower alkyl group or a phenyl group containing halogen, lower alkyl or trifluoromethyl group;

X represents halogen atom, carbomethoxy group, nitro group, or halogen or trifluoromethyl-substituted phenoxy group, being the same or different from one another;

A represents nitrogen or carbon atom; and n is an integer of 1 to 3, with the proviso that when n is 1, R is methyl, and A is carbon, that X is other than a bromine atom.

2. A process for preparing an oxazolinone derivative compound represented by the following formula I:

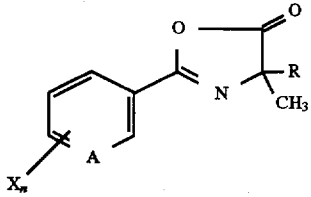

wherein, R represents a lower alkyl group or a phenyl group containing halogen, lower alkyl or trifluoromethyl group;

X represents halogen atom, carbomethoxy group, nitro group, or halogen or trifluoromethyl-substituted phenoxy group, being the same or different from one another;

A represents nitrogen or carbon atom; and n is an integer of 1 to 3, comprising the steps of:

condensating an α-amino acid represented by the following formula II:

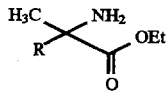

wherein R represents a lower alkyl group or a pheny group containing halogen, lower alkyl or trifluoromethyl group, with an acid chloride represented by the following formula III:

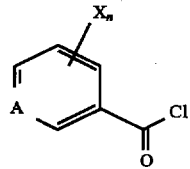

wherein X represents halogen atom, carbomethoxy group, nitro group, or halogen or trifluoromethyl-substituted phenoxy group, being the same or different from one another, to give an acyl α-amino acid represented by the following formula IV:

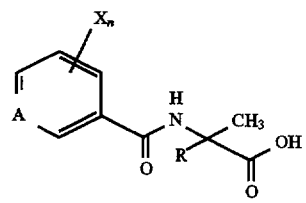

wherein, R is as defined above, A represents nitrogen or carbon atom, and n is an integer of 1 to 3;

reacting the acyl α-amino acid with anhydrous acetic acid; and dehydrating the resulting adduct.

3. An oxazolinone derivative compound in accordance with claim 1, wherein A is nitrogen.

4. An oxazolinone derivative compound in accordance with claim 1, wherein R is a phenyl group containing halogen, lower alkyl or trifluoromethyl group.

5. An oxazolinone derivative compound in accordance with claim 1, wherein one X is phenoxy substituted with one or two members selected from the group consisting of halogen and trifluoromethyl.

6. A composition comprising an herbicidally effective amount of a compound of formula I:

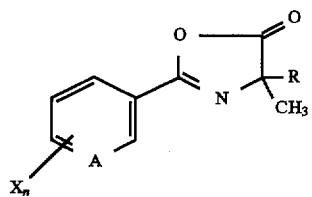

wherein, R represents a lower alkyl group or a phenyl group containing halogen, lower alkyl or trifluoromethyl group;

X represents halogen atom, carbomethoxy group, nitro group, or halogen or trifluoromethyl-substituted phenoxy group, being the same or different from one another;

A represents nitrogen or carbon atom; and n is an integer of 1 to 3, in combination with an herbicidel carrier.

* * * * *